(12) United States Patent
Barberousse et al.

(10) Patent No.: US 7,470,671 B2
(45) Date of Patent: Dec. 30, 2008

(54) THIOXYLOSE COMPOUNDS, PREPARATION METHOD THEREOF, PHARMACEUTICAL COMPOSITIONS CONTAINING SAME AND USE THEREOF IN THERAPEUTICS

(75) Inventors: Véronique Barberousse, Hauteville-les-Dijon (FR); Soth Samreth, Daix (FR); Benaïssa Boubia, Saint Apollinaire (FR); François Bellamy, Saulon-la-Rue (FR); Vincent Peyrou, Hauteville les Dijon (FR)

(73) Assignee: Laboratoire Fournier, Dijon (FR)

( * ) Notice: Subject to any disclaimer, the term of this patent is extended or adjusted under 35 U.S.C. 154(b) by 237 days.

(21) Appl. No.: 10/572,999

(22) PCT Filed: Sep. 24, 2004

(86) PCT No.: PCT/FR2004/002409

§ 371 (c)(1),
(2), (4) Date: Mar. 23, 2006

(87) PCT Pub. No.: WO2005/030785

PCT Pub. Date: Apr. 7, 2005

(65) Prior Publication Data

US 2007/0054955 A1    Mar. 8, 2007

(30) Foreign Application Priority Data

Sep. 25, 2003    (FR) .................................. 03 11264

(51) Int. Cl.
*A61K 31/70*    (2006.01)
*A61K 31/7042*    (2006.01)
*C07H 17/02*    (2006.01)

(52) U.S. Cl. ........................ 514/27; 514/25; 514/432; 536/17.6; 536/17.5; 536/17.9; 536/18.5; 536/55.3; 549/28

(58) Field of Classification Search ................ 536/17.6, 536/17.5, 17.9, 18.5, 55.3; 514/27, 25, 432; 549/28

See application file for complete search history.

(56) References Cited

U.S. PATENT DOCUMENTS

| 4,877,808 A | 10/1989 | Samreth et al. |
| 5,100,913 A | 3/1992 | Samreth et al. |
| 5,101,048 A | 3/1992 | Bajgrowicz et al. |

FOREIGN PATENT DOCUMENTS

| EP | 0 051 023 A1 | 5/1982 |
| EP | 0 421 829 A1 | 4/1991 |

*Primary Examiner*—Shaojia Anna Jiang
*Assistant Examiner*—Michael C Henry
(74) *Attorney, Agent, or Firm*—Merchant & Gould P.C.

(57) ABSTRACT

The invention relates to novel 5-thioxylose compounds, preferably derivatives of the 5-thioxylopyranose type, to the method for their preparation and to their use as active principles of drugs intended especially for the treatment or prevention of thromboses or cardiac insufficiency.

12 Claims, No Drawings

THIOXYLOSE COMPOUNDS, PREPARATION METHOD THEREOF, PHARMACEUTICAL COMPOSITIONS CONTAINING SAME AND USE THEREOF IN THERAPEUTICS

The present invention relates to novel 5-thioxylose compounds, preferably derivatives of the 5-thioxylopyranose type, to the method for their preparation and to their use as active principles of drugs intended especially for the treatment or prevention of thromboses.

PRIOR ART

D-xylose derivatives are already known e.g. from EP 051 023 B 1, U.S. Pat. No. 4,877,808, EP 421 829 B1 or the publication J. Med. Chem., vol. 36, no. 7, pp 898-903. The compounds described in these documents are useful for reducing the risks of venous thrombosis in humans. The mechanism of action of these compounds seems to be an effect on the plasmatic glycosarninoglycans (J. Biol. Chem., vol. 270, no. 6, pp 2662-68; Thromb. Haemost., 1999, 81, pp 945-950).

The majority of the compounds described are derivatives resulting from the coupling of a sugar with an aromatic derivative, especially a variously substituted benzene ring. The aglycone part of these compounds is generally of hydrophobic character. "Aglycone part" is understood as meaning the non-carbohydrate part of these compounds. Consequently, although the compounds of the prior art have the advantage of possessing a good activity when administered orally, they are practically unusable when administration by injection is preferable or unavoidable.

SUBJECT OF THE INVENTION

It has now been discovered that thioxylose derivatives of which the aglycone exhibits a more hydrophilic character have a good antithrombotic activity and are capable of being administered either orally or by injection.

DESCRIPTION

The novel compounds according to the invention are characterized in that they are selected from:
a) the compounds of the formula

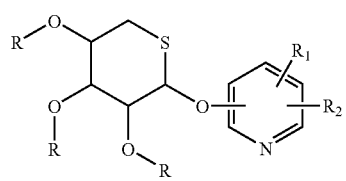

I in which:
the pentapyranosyl group is a 5-thio-β-D-xylopyranosyl group or a 5-thio-β-L-xylopyranosyl group,
R is a hydrogen atom, a $C_2$-$C_6$ acyl group, an acetyl group substituted by a nitrogen heterocycle, or a group —COOR',
$R_1$ and $R_2$ independently of one another are each a hydrogen atom, a halogen atom, a cyano, nitro or trifluoromethyl group, a $C_1$-$C_4$ alkyl group optionally substituted by an aromatic ring, a group —COOR', a group —CH$_2$—NR'R", a $C_1$-$C_4$ alkoxy group, a group —NH—CO—R' or a group —NH—SO$_2$—R', and
R' and R" independently are each a $C_1$-$C_4$ alkyl group; and
b) their addition salts, oxides or quaternary ammonium salts.

The invention further relates to a method of preparing the compounds of formula I and their addition salts, oxides or quaternary ammonium salts.

The invention further relates to the compounds of formula I for their use as pharmacologically active substances.

In particular, the invention relates to the use of at least one substance selected from the compounds of formula I and their non-toxic addition salts, oxides or quaternary ammonium salts for the preparation of a drug that is useful in human or animal therapeutics and intended for the prevention or treatment of thromboses, especially venous thromboses. As the compounds according to the invention are active by a mode of action that involves glycosaminoglycans, they may be useful as active principles of a drug intended for the treatment or prevention of any other disease in which glycosaminoglycans are implicated.

DETAILED DESCRIPTION

In formula I, $C_1$-$C_4$ alkyl group is understood as meaning a linear, branched or cyclic hydrocarbon chain having from 1 to 4 carbon atoms, examples of $C_1$-$C_4$ alkyl groups being particularly methyl, ethyl, propyl, butyl, 1-methylethyl, 1,1-dimethylethyl, 1-methylpropyl, 2-methylpropyl, cyclopropyl or cyclopropylmethyl groups.

Alkyl group optionally substituted by an aromatic ring is understood as meaning e.g. a phenylmethyl (benzyl) or phenylethyl group.

Halogen is understood as meaning a fluorine, chlorine, bromine or iodine atom, preferably a chlorine, fluorine or bromine atom.

$C_2$-$C_6$ acyl groups are understood as meaning acetyl, propionyl, butanoyl, pentanoyl or hexanoyl groups or their homologs in which the chain can be branched.

$C_1$-$C_4$ alkoxy group is understood as meaning a linear, branched or cyclic hydrocarbon chain having from 1 to 4 carbon atoms which is bonded via an oxygen atom. Examples of $C_1$-$C_4$ alkoxy groups which may be mentioned are methoxy, ethoxy, propoxy, butoxy, 1-methylethoxy, 1,1-dimethylethoxy, 1-methylpropoxy, 2-methylpropoxy or cyclopropylmethoxy groups.

Acetyl group substituted by a nitrogen heterocycle is understood as meaning e.g. a (1-piperidinyl)acetyl group or a (1-pyrrolidinyl)acetyl group.

Oxides are understood as meaning the N-oxide derivatives of the pyridine ring.

Quaternary ammonium salts are understood as meaning the ammonium salts resulting from reaction of the pyridine nitrogen with e.g. a halogen-containing compound, said reaction leading to the formation of a pyridinium halide.

Addition salts are understood as meaning the addition salts obtained by reacting a compound of formula I with a mineral or organic acid, pharmaceutically acceptable addition salts being preferred. The hydrates or solvates of the compounds of formula I or of the salts of the compounds of formula I also form an integral part of the invention.

Among the mineral acids that are suitable for salifying a basic compound of formula I, hydrochloric, hydrobromic, phosphoric and sulfuiric acids are preferred. Among the organic acids that are suitable for salifying a basic compound of formula I, methanesulfonic, benzenesulfonic, toluenesulfonic, maleic, fumaric, oxalic, citric, tartaric, lactic and trifluoroacetic acids are preferred.

Preferred compounds of formula I above are those in which:

the pentapyranosyl group is a 5-thio-β-D-xylopyranosyl group or a 5-thio-β-L-xylopyranosyl group, R is a hydrogen atom, a $C_2$-$C_6$ acyl group or a group —COOR', R' is a $C_1$-$C_3$ alkyl group, and $R_1$ and $R_2$ independently of one another are each a hydrogen atom, a halogen atom, a cyano, nitro or trifluoromethyl group or a $C_1$-$C_4$ alkyl group optionally substituted by an aromatic ring.

Very particularly preferred compounds according to the present invention are those in which $R_1$ and $R_2$ are a hydrogen atom and the pentapyranosyl group is 5-thio-β-D-xylopyranosyl.

Other preferred compounds according to the present invention are those in which R is the hydrogen atom, the group —COCH$_3$, the group —COOCH$_3$ or the group —COOC$_2$H$_5$.

Very particularly preferred compounds according to the present invention are those in which the pentapyranosyl group is in the 3-position of the pyridine heterocycle.

The compounds of formula I according to the invention can be prepared by the glycosylation methods known to those skilled in the art, especially:

a) HELFERICH's method described in the book "The Carbohydrate, Chemistry and Biochemistry", 2nd edition, Academic Press, New York-London 1972, volume IA, pages 292-294, in which a peracetylated sugar is condensed with a hydroxylated aromatic heterocycle in the presence of a Lewis acid;

b) KOENIGS-KNORR's method (idem, pages 295-299), in which a halogenated acylose is condensed with a hydroxyl group of phenolic character in the presence of a proton acceptor such as mercuric cyanide, silver imidazolate or silver trifluoromethylsulfonate; and c) SCHMIDT's method, in which an osyl trichloroacetimidate is condensed with a hydroxylated aromatic heterocycle in the presence of a Lewis acid such as trimethylsilyl trifluoromethanesulfonate or boron trifluoride etherate.

The compounds of formula I are preferably prepared by methods derived from the methods referred to above.

In a first, general method, the steps performed consist in:

a) reacting a pyridinol of the formula

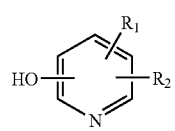

II in which:

$R_1$ and $R_2$ independently of one another are each a hydrogen atom, a halogen atom, a cyano, nitro or trifluoromethyl group, a $C_1$-$C_4$ alkyl group optionally substituted by an aromatic ring, a group —COOR', a group —CH$_2$—NR'R", a $C_1$-$C_4$ alkoxy group, a group —NH—CO—R' or a group —NH—SO$_2$—R', and R' and R" independently are each a $C_1$-$C_4$ alkyl group, with a 5-thioxylopyranose derivative of the formula

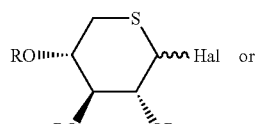

(III-D)

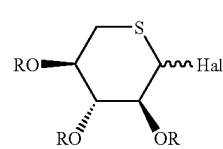

(III-L)

in which Hal is a halogen, preferably bromine, and R is a $C_2$-$C_6$ acyl group, preferably the acetyl group, in an aprotic solvent such as acetonitrile or toluene, in the presence of a silver salt, especially silver oxide or imidazolate, or a zinc salt (especially the oxide or chloride), in an anhydrous medium, at a temperature of between 25 and 80° C., for 1 to 10 hours, to give the compound of the formula

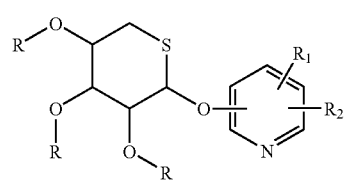

I in which the pentapyranose group is D- or L-5-thioxylopyranose and R, $R_1$ and $R_2$ are as defined in the starting compounds;

b) if necessary, reacting the compound of formula I obtained above with a solution of ammonia in methanol in order to deacylate it and thereby replace the acyl group with hydrogen atoms to give the compound of the formula

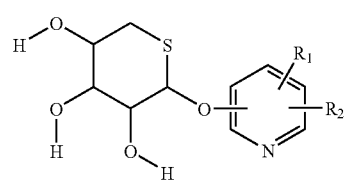

Ia in which $R_1$ and $R_2$ are as defined above; and c) if necessary, reacting one of the compounds obtained above, I or Ia, with an acid, by methods known to those skilled in the art, to give the corresponding addition salt.

As a variant of step b) described above, the replacement of the acyl group with a hydrogen atom can be effected by reaction with a metal alcoholate, preferably sodium methylate, in methanol, at a temperature of between 0 and 30° C., for 0.5 to 2 hours, to give the compound of formula Ia from the compound of formula I in which R is a $C_2$-$C_6$ acyl group.

In a second method, the compounds of formula I can be obtained by reacting the tetra-O-acetyl-5-thioxylopyranose of the formula

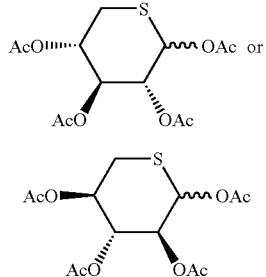

in which Ac is the acetyl group, with a compound of the formula

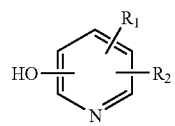
II in which:

R$_1$ and R$_2$ independently of one another are each a hydrogen atom, a halogen atom, a cyano, nitro or trifluoromethyl group, a C$_1$-C$_4$ alkyl group optionally substituted by an aromatic ring, a group —COOR', a group —CH$_2$—NR'R", a C$_1$-C$_4$ alkoxy group, a group —NH—CO—R' or a group —NH—SO$_2$—R', and R' and R" independently are each a C$_1$-C$_4$ alkyl group, in an aprotic solvent such as dichloromethane, in the presence of a catalyst of the Lewis acid type, e.g. tin tetrachloride, at a temperature of between 20 and 60° C., for

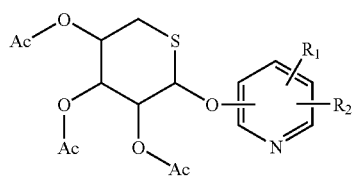
Ib in which R$_1$ and R$_2$ are as defined in the starting compounds.

The compound of formula Ib can then be reacted according to the protocol described in the previous method to give the unsubstituted pyranosyl compound and/or the salt with an acid.

According to another mode of preparing the compounds of formula I, a thioxylose derivative of the formula

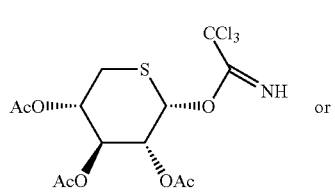
(V-D)

or

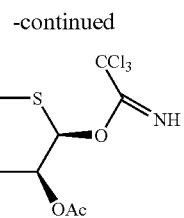
(V-L)

in which Ac is the acetyl group, is reacted with a compound of the formula

II

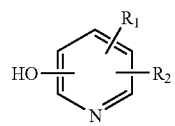

in which:

R$_1$ and R$_2$ independently of one another are each a hydrogen atom, a halogen atom, a cyano, nitro or trifluoromethyl group, a C$_1$-C$_4$ alkyl group optionally substituted by an aromatic ring, a group —COOR', a group —CH$_2$—NR'R", a C$_1$-C$_4$ alkoxy group, a group —NH—CO—R' or a group —NH—SO$_2$—R', and R' and R" independently are each a C$_1$-C$_4$ alkyl group, in an aprotic solvent such as dichloromethane, in the presence of a catalyst such as trimethylsilyl trifluoromethanesulfonate, at a temperature of between –25° C. and room temperature, for 1 to 5 hours, to give the thioxylopyranoside of the formula Ib

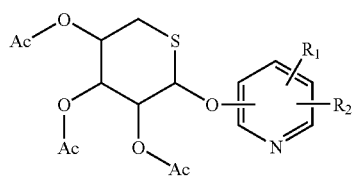

in which R$_1$ and R$_2$ are as defined in the starting compounds.

The resulting compound of formula Ib can then be reacted as above to give the unsubstituted pyranosyl compounds and/or the acid salts.

The compounds of formula I in which R is a group —COOR' can be obtained from the compounds of formula Ia by reaction with a pyrocarbonate of the formula

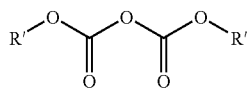

in which R' is a C$_1$-C$_4$ alkyl group, the reaction being carried out in an aprotic solvent such as acetonitrile, in the presence of an aprotic base such as 4-(dimethylamino)pyridine (DMAP).

The N-oxide derivatives can be obtained by coupling a pyridinol N-oxide of formula IIa:

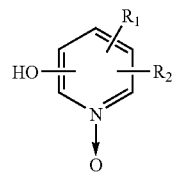

with a 5-thioxylopyranose of formula III-D or III-L according to the procedure described above for the first general method.

The quaternary ammonium salts can be obtained by reacting a compound of formula I with an appropriate organic halide according to the conventional procedures well known to those skilled in the art.

In general, when it is desired to obtain a β-D-5-thioxylopyranose derivative, it is preferable to use 2,3,4-tri-O-acetyl-5-thio-α-D-xylopyranosyl bromide or tetra-O-acetyl-5-thio-α-D-xylopyranose.

The glycosylation reactions described above most often lead to a mixture of the isomers of α and β configuration and it is generally necessary to optimize the operating conditions in order to obtain proportions that favor the isomer of β configuration. For this reason it may be necessary to carry out purifications, either by recrystallization or by chromatography, in order to obtain the pure β isomer.

The Examples which follow are intended to illustrate the invention without in any way limiting its scope. The melting points are measured on a Koffler bench and the nuclear magnetic resonance spectral values are characterized by the chemical shift calculated relative to TMS, by the number of protons associated with the signal, and by the shape of the signal (s for singlet, d for doublet, t for triplet, q for quadruplet, m for multiplet). The operating frequency and the solvent used are indicated for each compound.

Preparation I

N-(5-methoxy-2-pyridinyl)methanesulfonamide

A solution of 10.7 g (86 mmol) of 5-methoxy-2-pyridinamine in 55 ml of dichloromethane is cooled to 0° C. and 72 ml (144 mmol) of a 2 M solution of methanesulfonic anhydride in dichloromethane are added gradually. The reaction mixture is stirred for 6 hours at room temperature and sodium bicarbonate solution is then added in a sufficient amount to bring the pH to about 9. The mixture obtained is concentrated under reduced pressure, the residue is taken up in 160 ml of ethanol at 50° C., the mixture obtained is dried and filtered and the filtrate is concentrated under reduced pressure. The residue is triturated in 50 ml of cold ethanol and the solid obtained is filtered off, rinsed with a little ethanol on the filter and then dried to give 8.7 g of the expected product in the form of a white powder (yield=50%).
M.p.=156-158° C.

Preparation II

N-(5-hydroxy-2-pyridinyl)methanesulfonamide

A solution of 8.7 g (43 mmol) of the compound obtained according to Preparation I in 90 ml of dichloromethane is prepared and 12.2 ml (129 mmol) of boron tribromide are added gradually. The reaction mixture is stirred for 3 hours at the reflux point of the solvent and then concentrated under reduced pressure; 200 ml of water are added to the evaporation residue and the mixture obtained is neutralized by adding sodium hydroxide solution in a sufficient amount to bring the pH to about 7. The precipitate obtained is filtered off, rinsed with water on the filter and then triturated in 250 ml of hot ethanol; after cooling, the solid is filtered off, rinsed with 60 ml of ethanol on the filter and then dried to give 6.55 g of the expected product in the form of a white powder (yield=80%).
M.p.=246-247° C.

Preparation III 4-(Trifluoromethyl)-3-pyridinol

A solution of 2 g (12.34 mmol) of 3-amino-4-(trifluoromethyl)pyridine in 28 ml of 50% sulfuric acid is cooled to −5° C. and a solution of 1.03 g (14.8 mmol) of sodium nitrite in 10 ml of water is added slowly. The mixture is left to return to room temperature and stirring is continued for 30 min. 25 ml of concentrated sulfuric acid are then added and the reaction mixture is stirred at 100-110° C. for 2 hours. After cooling, the reaction medium is neutralized by adding saturated sodium bicarbonate solution to pH 6-7, and the mixture is extracted with ethyl acetate. The organic phase obtained is washed with water, dried over magnesium sulfate and concentrated under reduced pressure to give 1.92 g of the expected compound in the form of a brown powder (yield=95%).
M.p.=112-114° C.

Preparation IV

6-Cyano-3-pyridinol

A solution of 1 g (8.06 mmol) of 3-amino-6-cyanopyridine in 12 ml of water and 1.2 ml of sulfuric acid is cooled to 0° C. and 1 g (14.5 mmol) of sodium nitrite is added slowly. The reaction mixture is left to return to room temperature and then stirred at 100° C. for 3 hours. It is left to stand overnight in a refrigerator. The precipitate formed is filtered off and washed with iced water. The expected product also present in the filtrate is extracted with ethyl acetate and combined with the previous precipitate. This crude product is purified by chromatography on silica gel using a dichloromethane/methanol mixture (98/2; v/v) as the eluent to give 613 mg of the expected compound in the form of a brown powder (yield=63%).
M.p.=191-194° C.

Preparation V

6-Cyano-5-fluoro-3-pyridinol

A mixture of 2.94 g (20 mmol) of 6-chloro-5-fluoro-3-pyridinol, 360 mg (0.4 mmol) of tris(benzylideneacetone)dipalladium(0), 440 mg (0.8 mmol) 1,1'-bis(diphenylphosphino)ferrocene, 156 mg (2.4 mmol) of zinc powder and 1.4 g (12 mmol) of zinc cyanide in 40 ml of N,N-dimethylacetamide is prepared and the reaction mixture is then stirred at 140° C. for 5 hours. It is left to stand overnight at room temperature. 40 ml of 2 N aqueous ammonia are added slowly and the pH is then adjusted to about 4.5 with 5 N hydrochloric acid. The mixture is extracted 3 times with 100 ml of ethyl acetate and the organic phase obtained is dried over magnesium sulfate and concentrated under reduced pressure. The evaporation residue is purified by chromatography on silica gel using a methylcyclohexane/ethyl acetate mixture (in a gradient of 8/2 to 5/5; v/v) as the eluent to give 1.8 g of the expected compound in the form of an orange oil (yield=67%).

NMR (300 MHz, DMSO) δ=8.16 (s, 1H); 7.32 (d, 1H).

Preparation VI

6-Cyano-2-methyl-3-aminopyridine

A mixture of 3.5 g (18.6 mmol) of 6-bromo-2-methyl-3-aminopyridine, 352 mg (0.37 mmol) of tris(benzylideneacetone)dipalladium(0), 532 mg (0.92 mmol) of 1,1'-bis(diphenylphosphino)ferrocene, 146 mg (2.2 mmol) of zinc powder and 1.4 g (12 mmol) of zinc cyanide in 70 ml of N,N-dimethylacetamide is prepared and the reaction mixture is then stirred at 20° C. for 22 hours. It is diluted with 200 ml of ethyl acetate and washed with 2 N ammonium chloride solution. (Decantation is obtained only after filtration of the mixture on a filter aid of the Celite type.) The organic phase obtained is washed with sodium chloride solution, dried over magnesium sulfate and concentrated under reduced pressure. The evaporation residue is purified by chromatography on silica gel using a dichloromethane/ethyl acetate mixture (9/1; v/v) as the eluent to give 1.6 g of the expected compound in the form of a yellow powder (yield=65%).

M.p.=192-196° C.

Preparation VII

6-Cyano-2-Methyl-3-Pyridinol

By following a procedure analogous to Preparation IV and starting from the compound obtained according to Preparation VI, the expected compound is obtained in the form of a yellow powder (yield=50%).

M.p.=201-205° C.

Preparation VIII

5-Fluoro-3-pyridinol N-oxide

A solution of 1.5 g (13.26 mmol) of 5-fluoro-3-pyridinol in 8 ml of acetic acid is heated to 70° C. and 1.25 ml (14.6 mmol) of 35% hydrogen peroxide are added gradually. The reaction mixture is stirred for 15 hours at 70° C. and then concentrated under reduced pressure; 50 ml of cold water are added to the evaporation residue and the mixture is stirred for 1 hour. The precipitate obtained is filtered off, rinsed with water and with a minimum amount of cold ethyl acetate on the filter and then dried to give 930 mg of the expected product in the form of a white powder (yield=55%).

M.p.=197° C.

Preparation IX

5-Fluoro-2-Cyano-3-Pyridinol

A solution of 890 mg (6.89 mmol) of the compound obtained according to Preparation VIII, 1.74 g (17.23 mmol) of triethylamine and 2.39 g (24.1 mmol) of trimethylsilyl cyanide in 5 ml of acetonitrile is refluxed gently for 16 hours. The reaction mixture is concentrated under reduced pressure and 50 ml of ethyl acetate are added to the evaporation residue. The organic phase obtained is washed with sodium chloride solution and then dried over magnesium sulfate and concentrated under reduced pressure. The evaporation residue is purified by chromatography on silica gel using a dichloromethane/methanol mixture (98/2; v/v) as the eluent. The oily product resulting from chromatography is triturated in ethyl ether and the expected compound is left to crystallize in the form of an off-white solid (yield=18%).

M.p.=201° C.

EXAMPLE 1

3-Pyridinyl 2,3,4-Tri-O-Acetyl-5-Thio-β-D-Xylopyranoside 2.15 g (15.8 mmol) of anhydrous zinc chloride, 1 g (10.5 mmol) of 3-hydroxy-pyridine and 3 g of 13X molecular sieve are mixed in 10 ml of toluene and 10 ml of acetonitrile. The mixture is stirred for 15 min and then heated to 60° C. and placed in the dark. 2.2 g (12.6 mmol) of silver imidazolate and 4.5 g (12.6 mmol) of 2,3,4-tri-O-acetyl-5-thio-α-D-xylopyranosyl bromide are added. The mixture is stirred for 18 hours at 60° C. and then filtered. 50 ml of ethyl acetate are added to the filtrate and the organic phase is washed with 1 N sodium hydroxide solution. (A flocculation is observed, which is removed by filtration on a bed of filter aid.) The organic phase is separated off, washed with water and then dried over magnesium sulfate and concentrated under reduced pressure. The residue is crystallized by adding ethyl ether; the crystals obtained are filtered off and dried to give 1.45 g of the expected product in the form of white crystals (yield=37%).

M.p.=147° C.

$[\alpha]_D^{24}=-84°$ (c=0.10; CHCl$_3$).

EXAMPLE 1A

3-Pyridinyl 2,3,4-tri-O-acetyl-5-thio-β-D-Xylopyranoside Methanesulfonate 0.5 g (1.35 mmol) of the compound obtained according to Example 1 is dissolved in 100 ml of ethyl acetate, and 50 ml of ethyl ether and a solution of 0.13 g (1.35 mmol) of methanesulfonic acid in 1 ml of dichloromethane and 0.2 ml of methanol are added. The reaction mixture is stirred for 10 minutes and the precipitate is separated from the liquid phase and then triturated in ethyl ether. The crystals formed are filtered off, rinsed and dried to give 0.5 g of the expected salt in the form of white crystals (yield=80%).

M.p.=104° C.

$[\alpha]_D^{20}=-82°$ (c=0.32; CH$_3$OH).

EXAMPLE 2

3-Pyridinyl 5-Thio-β-D-Xylopyranoside 1.35 g (3.6 mmol) of the compound obtained according to Example 1 are mixed with 50 ml of a 7 mol/l solution of ammonia in methanol and this reaction medium is stirred for 2 hours at room temperature. The mixture is then concentrated under reduced pressure and the crystals obtained are taken up in 30 ml of methanol under reflux. After cooling to 10° C., the crystals are filtered off and dried to give 0.75 g of the expected product in the form of white crystals (yield=84%).

M.p.=219° C.

$[\alpha]_D^{22}=-99°$ (c=0.445; DMSO).

EXAMPLE 2A

3-Pyridinyl 5-Thio-β-D-Xylopyranoside Methanesulfonate

A suspension of 10 g (41.1 mmol) of the compound obtained according to Example 2 in 100 ml of methanol is prepared and a solution of 2.8 ml (4.15 g; 43.1 mmol) of methanesulfonic acid in 40 ml of methanol is added rapidly. The mixture is stirred for 2 hours at room temperature. A solution forms, followed by a precipitate. The solid obtained is filtered off and crystallized from about 200 ml of a methanol/water mixture (95/5) to give 9 g of the expected salt in the form of a beige powder (yield=64%).

M.p.=168° C.

$[\alpha]_D^{29}$=−110° (c=0.3; H$_2$O).

EXAMPLE 2B

3-Pyridinyl 5-Thio-β-D-Xylopyranoside Neutral Sulfate

A suspension of 0.5 g (2.05 mmol) of the compound obtained according to Example 2 in 2 ml of methanol is prepared and 30 ml of water and 52.5 μl of sulfuric acid are added. The mixture is stirred for 15 min at room temperature and then frozen and lyophilized. The lyophilizate obtained is taken up in 25 ml of water and lyophilized again to give the expected product in the form of a white powder (yield=95%).

M.p.=80° C.

$[\alpha]_D^{28}$=−48.8° (c=0.5; DMSO).

EXAMPLE 2C

3-Pyridinyl 5-Thio-β-D-Xylopyranoside Hydrochloride

A suspension of 5 g (20.55 mmol) of the compound obtained according to Example 2 in 20.5 ml of an N solution of hydrogen chloride in ethyl ether is prepared. 2 ml of methanol are then added. A gum forms, which crystallizes. The mixture is stirred for 1 hour and the precipitate is then filtered off, dried and recrystallized from 95% ethanol. After drying, the expected compound (containing one mol of ethanol per mol of salt) is obtained in the form of beige crystals (yield=90%). The product is taken up in solution in water and lyophilized to give the expected product in the form of a beige powder.

M.p.=120° C.

$[\alpha]_D^{23}$=−149° (c=0.2; H$_2$O).

EXAMPLE 2D

3-Pyridinyl 5-Thio-β-D-Xylopyranoside Hydrobromide

By following a procedure analogous to Example 2C and adding a solution of hydrogen bromide in ethyl ether to a suspension of the compound according to Example 2 in methanol, the expected product is obtained in the form of a beige powder (yield=30%).

$[\alpha]_D^{28}$=−73° (c=0.57; DMSO).

EXAMPLE 3

3-Pyridinyl 2,3,4-Tri-O-Acetyl-5-Thio-β-L-Xylopyranoside

By following a procedure analogous to Example 1 and starting from 2,3,4-tri-O-acetyl-5-thio-α-L-xylopyranosyl bromide, the expected product is obtained in the form of an oil (yield=10%) after purification by chromatography on silica gel using ethyl acetate as the eluent.

$^1$H NMR (300 MHz; CDCl$_3$) δ=8.40 (d, 1H); 8.33 (dd, 1H); 7.38 (m, 1H); 7.26 (m, 1H); 5.52 (t, 1H); 5.14 (m, 3H); 3.00 (m, 1H); 2.68 (m, 1H); 2.06 (m, 9H).

EXAMPLE 4

3-Pyridinyl 5-Thio-β-L-Xylopyranoside

By following a procedure analogous to Example 2 and starting from the compound obtained according to Example 3, the expected compound is obtained in the form of an off-white powder (yield=27%).

M.p.=216° C.

$[\alpha]_D^{32}$=+950 (c=0.36; DMSO).

EXAMPLE 5

2-Pyridinyl 2,3,4-Tri-O-Acetyl-5-Thio-β-D-Xylopyranoside

A solution of 0.5 g (5.2 mmol) of 2-hydroxypyridine in 20 ml of dichloromethane is prepared and 2.5 g (5.7 mmol) of 2,3,4-tri-O-acetyl-5-thio-α-D-xylopyranosyl trichloroacetimidate are added. The mixture is cooled to −20° C. and 2.7 ml of a 0.2 M solution of trimethylsilyl trifluoromethanesulfonate are added, with stirring. The reaction medium is stirred for 4 hours at 0° C., 0.5 ml of diisopropylethylamine is then added and the mixture is concentrated under reduced pressure. The evaporation residue is crystallized by adding an ethyl ether/methylcyclohexane mixture. The crude product is isolated and recrystallized from a methanol/water mixture to give 1.07 g of the expected product in the form of a beige powder (yield=55%).

M.p.=138° C.

$[\alpha]_D^{32}$=−66° (c=0.38; CHCl$_3$).

EXAMPLE 6

2-Pyridinyl 5-Thio-β-D-Xylopyranoside

By following a procedure analogous to Example 2 and starting from the compound obtained according to Example 5, the expected product is obtained in the form of white crystals (yield=78%).

M.p.=196° C.

$[\alpha]_D^{23}$=−73° (c=0.46; DMSO).

EXAMPLE 7

Pyridin-3-yl 2,3,4-Tri-O-Acetyl-5-Thio-β-D-Xylopyranoside N-Oxide

By following a procedure analogous to Example 1 and starting from 3-pyridinol N-oxide, the expected product is obtained in the form of a light beige powder (yield=10%).

M.p.=161° C.

$[\alpha]_D^{28}$=−96° (c=0.58; CHCl$_3$).

EXAMPLE 8

Pyridin-3-yl 5-Thio-β-D-Xylopyranoside N-Oxide 2.65 g (6.9 mmol) of the compound obtained according to Example 7 are dissolved in 50 ml of methanol, and 0.265 ml of an 8% solution of sodium methylate in methanol is added at room temperature. The reaction mixture is stirred for 30 min. Water is added to dissolve the precipitate formed, and IR 120 resin (acid form) is then added to bring the pH of the mixture to about 6. The resin is then removed by filtration and the filtrate is concentrated under reduced pressure. The residue obtained is crystallized from methanol, filtered off and then dissolved in 40 ml of hot water. The solution is filtered and then lyophilized to give 1.48 g of the expected compound in the form of a fine white solid (yield=83%).

M.p.=98° C.

$[\alpha]_D^{28}$=−90° (c=0.48; DMSO).

EXAMPLE 9

4-Pyridinyl 2,3,4-Tri-O-Acetyl-5-Thio-β-D-Xylopyranoside

By following a procedure analogous to Example 1 and starting from 4-hydroxy-pyridine, the expected product is obtained in the form of beige crystals (yield=12%).

M.p.=152-158° C.

$[\alpha]_D^{20}$=−73° (c=1.00; CHCl$_3$).

EXAMPLE 10

4-Pyridinyl 5-Thio-β-D-Xylopyranoside

By following a procedure analogous to Example 8 and starting from the compound obtained according to Example 9, the expected product is obtained in the form of an off-white powder (yield=59%).

M.p.=165-168° C.

$[\alpha]_D^{20}$=−94° (c=1.00; DMSO).

EXAMPLE 11

2-Methyl-3-Pyridinyl 2,3,4-Tri-O-Acetyl-5-Thio-β-D-Xylopyranoside 6 g (73.7 mmol) of zinc oxide, 2.6 g (19 mmol) of zinc chloride and 4 g of 4 Å molecular sieve are mixed. This mixture is desiccated perfectly and 2 g (18.3 mmol) of 2-methyl-3-pyridinol and 6.6 g (18.6 mmol) of 2,3,4-tri-O-acetyl-5-thio-α-D-xylopyranosyl bromide in 40 ml of toluene and 40 ml of acetonitrile are then added. The mixture is stirred at 60° C. for 18 hours and then filtered. The filtrate is concentrated under reduced pressure and the evaporation residue is purified by chromatography on silica gel using an ethyl acetate/hexane mixture (7/3 then 100% ethyl acetate; v/v) as the eluent to give the expected product in the form of a beige solid (yield=7%).

$^1$H NMR (300 MHz; CDCl$_3$) 2.04 (s, 3H); 2.06 (s, 3H); 2.07 (s, 3H); 2.42 (s, 3H); 2.70 (dd, 1H); 2.98 (dd, 1H); 5.16 (m, 3H); 5.77 (t, 1H); 7.12 (m, 1H); 7.37 (d, 1H); 8.19 (m, 1H).

EXAMPLE 12

2-Methyl-3-Pyridinyl 5-Thio-β-D-Xylopyranoside

By following a procedure analogous to Example 2 and starting from the compound obtained according to Example 11, the expected product is obtained in the form of a fine beige solid (yield=98%).

M.p.=187° C.

$[\alpha]_D^{23}$=−84° (c=0.2; DMSO).

EXAMPLE 13

2-(Phenylmethyl)-3-Pyridinyl 2,3,4-Tri-O-Acetyl-5-Thio-β-D-Xylopyranoside

By following a procedure analogous to Example 1 and starting from 2-(phenyl-methyl)-3-pyridinol, the expected product is obtained in the form of a white solid (yield=25%).

M.p.=163-166° C.

$[\alpha]_D^{20}$=−104° (c=1.00; CHCl$_3$).

EXAMPLE 14

2-(Phenylmethyl)-3-Pyridinyl 5-Thio-β-D-Xylopyranoside

By following a procedure analogous to Example 2 and starting from the compound obtained according to Example 13, the expected product is obtained in the form of an off-white powder (yield=54%).

M.p.=156° C.

$[\alpha]_D^{20}$=−97° (c=1.00; DMSO).

EXAMPLE 15

2-Ethyl-6-Methyl-3-Pyridinyl 2,3,4-Tri-O-Acetyl-5-Thio-β-D-Xylopyranoside

By following a procedure analogous to Example 1 and starting from 2-ethyl-6-methyl-3-pyridinol, the expected product is obtained in the form of a white powder (yield=19%).

M.p.=123-127° C.

$[\alpha]_D^{20}$=−84° (c=1.00; CHCl$_3$).

EXAMPLE 16

2-Ethyl-6-Methyl-3-Pyridinyl 5-Thio-β-D-Xylopyranoside

By following a procedure analogous to Example 8 and starting from the compound obtained according to Example 15, the expected product is obtained in the form of a white powder (yield=58%).

M.p.=172-174° C.

$[\alpha]_D^{20}$=−68° (c=1.00; DMSO).

EXAMPLE 17

5-Chloro-3-Pyridinyl 2,3,4-Tri-O-Acetyl-5-Thio-β-D-Xylopyranoside

By following a procedure analogous to Example 1 and starting from 5-chloro-3-pyridinol, the expected product is obtained in the form of a white powder (yield=29%).

M.p.=160° C.

$[\alpha]_D^{24}$=−73° (c=0.48; CHCl$_3$).

EXAMPLE 18

5-Chloro-3-Pyridinyl 5-Thio-β-D-Xylopyranoside

By following a procedure analogous to Example 1 and starting from the compound obtained according to Example 17, the expected product is obtained in the form of a white powder (yield=90%).

M.p.=184° C.

$[\alpha]_D^{24}$=−82° (c=0.47; DMSO).

EXAMPLE 19

2-Cyano-3-Pyridinyl 2,3,4-Tri-O-Acetyl-5-Thio-β-D-Xylopyranoside

A solution of 1.7 g (14.17 mmol) of 2-cyano-3-pyridinol in 30 ml of acetonitrile is prepared and 4.3 g (18.3 mmol) of silver oxide and 3 g of 13X molecular sieve are added in the dark. The mixture is stirred for 10 min at 50° C., 6.5 g (18.3 mmol) of 2,3,4-tri-O-acetyl-β-D-xylopyranoside bromide are then added and the reaction mixture is stirred for 18 hours at 50° C. It is then cooled to room temperature and filtered on a filter aid. The filtrate is diluted with ethyl acetate, washed with water, with N sodium hydroxide solution and then with water until the pH is neutral, and finally dried over magnesium sulfate and concentrated under reduced pressure. The residual oil is crystallized by adding ethyl ether to give 0.89 g of the expected product in the form of beige crystals (yield=16%).

$^1$H NMR (300 MHz; CDCl$_3$) δ: 8.43 (m, 1H); 7.53 (m, 2H); 5.49 (t, 1H); 5.30 (d, 1H); 5.19 (m, 2H); 3.18 (m, 1H); 2.76 (m, 1H); 2.10 (m, 9H).

The product contains a small proportion of α derivatives whose anomeric proton gives signals at δ=5.76 and δ=5.63.

EXAMPLE 20

2-Cyano-3-Pyridinyl 5-Thio-β-D-Xylopyranoside

By following a procedure analogous to Example 2 and starting from the compound obtained according to Example 19, the expected product is obtained in the form of white crystals (yield=60%).

M.p.=174° C.
$[α]_D^{23}$=−43 (c=0.30; DMSO).

EXAMPLE 21

6-Methyl-3-Pyridinyl 2,3,4-Tri-O-Acetyl-5-Thio-β-D-Xylopyranoside

By following a procedure analogous to Example 11 and starting from 6-methyl-3-pyridinol, the crude product is obtained, which is then purified by chromatography on silica gel using a dichloromethane/ethyl ether mixture (1/1; v/v) as the eluent, followed by recrystallization from ethyl acetate, to give the expected product in the form of a yellow solid (yield=20%).

M.p.=130° C.
$[α]_D^{22}$=−65° (c=0.17; CHCl$_3$).

EXAMPLE 22

6-Methyl-3-Pyridinyl 5-Thio-β-D-Xylopyranoside

By following a procedure analogous to Example 2 and starting from the compound obtained according to Example 21, the expected product is obtained in the form of white crystals (yield=80%).

M.p.=233° C.
$[α]_D^{22}$=−90° (c=0.155; CH$_3$OH).

EXAMPLE 23

Methyl 5-[(2,3,4-Tri-O-Acetyl-5-Thio-β-D-Xylopyranosyl)Oxy]-3-Pyridine-Carboxylate By following a procedure analogous to Example 1 and starting from methyl 5-hydroxy-3-pyridinecarboxylate, the expected product is obtained in the form of a beige solid (yield=7%).

M.p.=50° C.
$[α]_D^{24}$=−8° (c=0.3; CH$_3$OH).

EXAMPLE 24

Methyl 5-[(5-Thio-β-D-Xylopyranosyl)Oxy]-3-Pyridinecarboxylate

By following a procedure analogous to Example 2 and starting from the compound obtained according to Example 23, the expected product is obtained in the form of a fine beige powder (yield=99%).

M.p.=137° C.
$[α]_D^{24}$=−48° (c=0.3; CH$_3$OH).

EXAMPLE 25

2-Bromo-3-Pyridinyl 2,3,4-Tri-O-Acetyl-5-Thio-β-D-Xylopyranoside

By following a procedure analogous to Example 1 and starting from 2-bromo-3-pyridinol, the expected product is obtained in the form of a white powder (yield=40%).

M.p.=161° C.
$[α]_D^{22}$=−66° (c=1.8; CHCl$_3$).

EXAMPLE 26

2-Bromo-3-Pyridinyl 5-Thio-β-D-Xylopyranoside

By following a procedure analogous to Example 2 and starting from the compound obtained according to Example 25, the expected product is obtained in the form of a white powder (yield=85%).

M.p.=151° C.
$[α]_D^{22}$=−51° (c=0.16; DMSO).

EXAMPLE 27

2-Nitro-3-Pyridinyl 2,3,4-Tri-O-Acetyl-5-Thio-β-D-Xylopyranoside

By following a procedure analogous to Example 19 and starting from 2-nitro-3-pyridinol, the expected product is obtained in the form of an off-white powder (yield=28%).

M.p.=178° C.
$[α]_D^{22}$=−132° (c=0.25; CHCl$_3$).

EXAMPLE 28

6-Methyl-2-Nitro-3-Pyridinyl 2,3,4-Tri-O-Acetyl-5-Thio-β-D-Xylopyranoside

By following a procedure analogous to Example 1 and starting from 6-methyl-2-nitro-3-pyridinol, the expected product is obtained in the form of a white powder (yield=11%).

M.p.=154° C.
$[α]_D^{21}$=−92° (c=0.48; CHCl$_3$).

EXAMPLE 29

3-Pyridinyl 2,3,4-Tris-O-(2-Methylpropionyl)-5-Thio-β-D-Xylopyranoside

A solution of 0.6 g (2.4 mmol) of the compound obtained according to Example 2 in 25 ml of pyridine is prepared and 30 mg (0.24 mmol) of 4-(dimethylamino)-pyridine are added. 1.18 g (11 mmol) of 2-methylpropionyl chloride are then added at room temperature, with stirring. The reaction mixture is stirred for 1 hour at 60° C. and then diluted with 60 ml of toluene and concentrated under reduced pressure. The evaporation residue is purified by chromatography on silica gel using a toluene/ethyl acetate mixture (75/25; v/v) as the eluent to give 810 mg of the expected compound (yield=73%).

$^1$H NMR (300 MHz; DMSO) δ: 8.33 (m, 1H); 8.26 (m, 1H); 7.50 (m, 1H); 7.40 (m, 1H); 5.96 (d, 1H); 5.34 (m, 2H); 5.01 (m, 1H); 3.04 (m, 1H); 2.88 (m, 1H); 2.42 (m, 3H); 1.02 (m, 12H); 0.94 (t, 6H).

EXAMPLE 29A

3-Pyridinyl 2,3,4-Tris-O-(2-Methylpropionyl)-5-Thio-β-D-Xylopyranoside Methanesulfonate A solution of 802 mg (1.76 mmol) of the compound obtained according to Example 29 in 5 ml of ethyl acetate is prepared and 2 ml of ethyl ether are added, followed by a solution of 131 μl (1.78 mmol) of methanesulfonic acid in 4 ml of tetrahydrofuran. A white precipitate forms. The reaction mixture is stirred for 15 min and then cooled to 5° C. and filtered to give 768 mg of the expected salt in the form of a white powder (yield=81%).

M.p.=215° C.
$[\alpha]_D^{24}$=−70° (c=0.44; CH$_3$OH).

EXAMPLE 30

3-Pyridinyl 2,3,4-Tris-O-(3-Methylbutanoyl)-5-Thio-β-D-Xylopyranoside

By following a procedure analogous to Example 29 and starting from 3-methyl-butanoyl chloride, the expected product is obtained in the form of a white solid (yield=53%).

$^1$H NMR (300 MHz; DMSO) δ: 8.52 (m, 1H); 8.41 (m, 1H); 7.83 (m, 1H); 7.65 (m, 1H); 6.00 (d, 1H); 5.40 (t, 1H); 5.30 (t, 1H); 5.00 (m, 1H); 3.00 (m, 2H); 2.12 (m, 6H); 1.95 (m, 3H); 0.82 (m, 18H).

EXAMPLE 30A

3-Pyridinyl 2,3,4-Tris-O-(3-Methylbutanoyl)-5-Thio-β-D-Xylopyranoside Methanesulfonate By following a procedure analogous to Example 29A and starting from the compound obtained according to Example 30, the expected product is obtained in the form of a white powder (yield=59%).

M.p.=164° C.
$[\alpha]_D^{24}$=−68° (c=0.28; CH$_3$OH).

EXAMPLE 31

3-Pyridinyl 2,3,4-Tris-O-(Methoxycarbonyl)-5-Thio-β-D-Xylopyranoside

A suspension of 0.3 g (1.23 mmol) of the compound obtained according to Example 2 in 10 ml of acetonitrile and 10 ml of tetrahydrofuran is prepared and about 30 mg of 4-(dimethylamino)pyridine and 300 mg of 4 A molecular sieve are added. 0.8 ml (7.5 mmol) of dimethyl pyrocarbonate is then added. The mixture is stirred for 24 hours at room temperature and filtered. The filtrate is concentrated under reduced pressure and the residue is purified by chromatography on silica gel using an ethyl acetate/hexane mixture (7/3; v/v) as the eluent to give 0.25 g of the expected compound in the form of a white powder (yield=50%).

M.p.=62° C.
$[\alpha]_D^{23}$=−78° (c=0.15; CHCl$_3$).

EXAMPLE 31A

3-Pyridinyl 2,3,4-Tris-O-(Methoxycarbonyl)-5-Thio-β-D-Xylopyranoside Hydrochloride A solution of 560 mg (1.34 mmol) of the compound obtained according to Example 31 in 150 ml of anhydrous ethyl ether is prepared and 0.56 ml of a solution of hydrogen chloride in ethyl ether (2.3 N solution) is added. The salt precipitates in the form of a very fine solid, which is extracted with pure water. The aqueous phase is separated off and lyophilized to give 550 mg of the expected compound in the form of a white powder (yield=90%).

M.p.=155° C.
$[\alpha]_D^{22}$=−34° (c=0.55; DMSO).

EXAMPLE 31B

3-Pyridinyl 2,3,4-Tris-O-(Methoxycarbonyl)-5-Thio-β-D-Xylopyranoside Methanesulfonate A solution of 200 mg (0.48 mmol) of the compound obtained according to Example 31 is prepared and 50 mg (0.52 mmol) of a solution of methanesulfonic acid in 4 ml of ethyl ether and 0.2 ml of methanol are added. The precipitate formed is filtered off and taken up in solution in water, and the solution is lyophilized to give 230 mg of the expected salt in the form of a fine white solid (yield=96%).

M.p.=148° C.
$[\alpha]_D^{25}$=−68° (c=0.18; CH$_3$OH).

EXAMPLE 32

1-[[[(Dimethylamino)Carbonyl]oxy]Methyl]-3-[(5-Thio-β-D-Xylopyranosyl)Oxy]-Pyridinium Chloride 1 g (4.1 mmol) of the compound obtained according to Example 2 is mixed with 100 ml of acetonitrile. 0.62 g (4.1 mmol) of sodium iodide and 0.68 g (4.9 mmol) of chloromethyl dimethylaminoformate are added. The reaction mixture is stirred for 2 hours at room temperature and then filtered. The filter is rinsed with 20 ml of dichloromethane and 20 ml of methanol and the combined filtrates are percolated through a column of Dowex IX8-200 Cl$^-$ resin and then concentrated under reduced pressure. The evaporation residue is triturated in acetone. The solid formed is filtered off, taken up in solution in water and lyophilized to give 800 mg of the expected compound in the form of a fine beige solid (yield=51%).

M.p.=117IC.
$[\alpha]_D^{24}$=−77° (c=0.22; CH$_3$OH).

EXAMPLE 33

3-Pyridinyl 2,3,4-Tris-O-(2,2-Dimethylpropionyl)-5-Thio-β-D-Xylopyranoside Pivalate A solution of 1 g (4.11 mmol) of the compound obtained according to Example 2 in 20 ml of pyridine is prepared and 1 g of 4 A molecular sieve is added, followed by 7.6 ml (37 mmol) of trimethylacetic anhydride and 30 mg (0.24 mmol)

of 4-(dimethylamino)pyridine. The reaction mixture is refluxed for 2 hours and then stirred at room temperature for 24 hours. It is then filtered, the filter is rinsed with 20 ml of methanol and the filtrates are concentrated under reduced pressure. The crude product obtained is purified by chromatography on silica gel using a cyclohexane/ethyl acetate mixture (55/45; v/v) as the eluent to give 600 mg of the expected triester in the form of the trimethylacetic acid salt (pivalate). Yield=24% (white powder).

M.p.=140° C.

$[\alpha]_D^{25}$=−56° (c=0.50; CH$_3$OH).

EXAMPLE 34

6-Methyl-2-Pyridinyl 2,3,4-Tri-O-Acetyl-5-Thio-β-D-Xylopyranoside

By following a procedure analogous to Example 1 and starting from 6-methyl-2-pyridinol, the expected product is obtained in the form of a white powder (yield=10%).

M.p.=106° C.

$[\alpha]_D^{22}$=−50° (c=0.25; CHCl$_3$).

EXAMPLE 35

6-Methyl-2-Pyridinyl 5-Thio-β-D-Xylopyranoside

By following a procedure analogous to Example 2 and starting from the compound obtained according to Example 34, the expected product is obtained in the form of a white powder (yield=90%) after lyophilization.

M.p.=54° C.

$[\alpha]_D^{25}$=−63° (c=0.26; DMSO).

EXAMPLE 36

2-Chloro-3-Pyridinyl 2,3,4-Tri-O-Acetyl-5-Thio-β-D-Xylopyranoside

By following a procedure analogous to Example 1 and starting from 2-chloro-3-pyridinol, the expected product is obtained in the form of a white solid (yield=37%).

M.p.=160° C.

$[\alpha]_D^{21}$=−108° (c=0.43; CH$_2$Cl$_2$).

EXAMPLE 37

2-Chloro-3-Pyridinyl 5-Thio-β-D-Xylopyranoside

By following a procedure analogous to Example 8 and starting from the compound obtained according to Example 36, the expected product is obtained in the form of a white solid (yield=97%).

M.p.=153° C.

$[\alpha]_D^{23}$=−44° (c=0.44; DMSO).

EXAMPLE 38

2-(Dimethylaminomethyl)-3-Pyridinyl 2,3,4-Tri-O-Acetyl-5-Thio-β-D-Xylopyranoside By following a procedure analogous to Example 11 and starting from 2-dimethyl-aminomethyl-3-pyridinol, the expected product is obtained in the form of a yellow solid (yield=12%).

M.p.=105° C.

$[\alpha]_D^{21}$=−74° (c=0.41; CH$_2$Cl$_2$).

EXAMPLE 39

2-(Dimethylaminomethyl)-3-Pyridinyl 5-Thio-β-D-Xylopyranoside

By following a procedure analogous to Example 8 and starting from the compound obtained according to Example 38, the expected product is obtained in the form of a white solid (yield=90%).

M.p.=79° C.

$[\alpha]_D^{23}$=−48 (c=0.40; DMSO).

EXAMPLE 40

6-(Trifluoromethyl)-3-Pyridinyl 2,3,4-Tri-O-Acetyl-5-Thio-β-D-Xylopyranoside

By following a procedure analogous to Example 1 and starting from 6-trifluoro-methyl-3-pyridinol, the expected product is obtained in the form of a white powder (yield=28%).

M.p.=156° C.

$[\alpha]_D^{23}$=−6° (c=0.69; CHCl$_3$).

EXAMPLE 41

6-(Trifluoromethyl)-3-Pyridinyl 5-Thio-β-D-Xylopyranoside

By following a procedure analogous to Example 8 and starting from the compound obtained according to Example 40, the expected product is obtained in the form of a beige solid (yield=97%).

M.p.=170-175° C.

$[\alpha]_D^{23}$=−78 (c=0.40; DMSO).

EXAMPLE 42

5-Chloro-2-Cyano-3-Pyridinyl 2,3,4-Tri-O-Acetyl-5-Thio-β-D-Xylopyranoside

By following a procedure analogous to Example 1 and starting from 5-chloro-2-cyano-3-pyridinol, the expected product is obtained in the form of a white solid (yield=11%).

M.p.=171° C.

$[\alpha]_D^{23}$=−137° (c=0.17; CH$_2$Cl$_2$).

EXAMPLE 43

5-Chloro-2-Cyano-3-Pyridinyl 5-Thio-β-D-Xylopyranoside

By following a procedure analogous to Example 8 and starting from the compound obtained according to Example 42, the expected product is obtained in the form of an off-white solid (yield=52%).

M.p.=122° C.

$[\alpha]_D^{20}$=−71° (c=0.28; CH$_3$OH).

EXAMPLE 44

4-Cyano-2-Methyl-3-Pyridinyl 2,3,4-Tri-O-Acetyl-5-Thio-β-D-Xylopyranoside

By following a procedure analogous to Example 5 and starting from 4-cyano-2-methyl-3-pyridinol, the expected product is obtained in the form of a brown solid (yield=59%).

M.p.=109-113° C.

$[\alpha]_D^{23}$=−4.8° (c=0.50; CH$_2$Cl$_2$).

EXAMPLE 45

4-Cyano-2-Methyl-3-Pyridinyl 5-Thio-β-D-Xylopyranoside

By following a procedure analogous to Example 8 and starting from the compound obtained according to Example 44, the expected product is obtained in the form of a pale pink solid (yield=45%).
M.p.=161° C.
$[\alpha]_D^{23}$=−2.5° (c=0.50; $CH_3OH$).

EXAMPLE 46

2-Fluoro-6-Methyl-3-Pyridinyl 2,3,4-Tri-O-Acetyl-5-Thio-β-D-Xylopyranoside

By following a procedure analogous to Example 1 and starting from 2-fluoro-6-methyl-3-pyridinol, the expected product is obtained in the form of a white powder (yield=7%).
M.p.=139° C.
$[\alpha]_D^{28}$=−98° (c=0.25; $CHCl_3$).

EXAMPLE 47

2-Fluoro-6-Methyl-3-Pyridinyl 5-Thio-β-D-Xylopyranoside

By following a procedure analogous to Example 2 and starting from the compound obtained according to Example 46, the expected product is obtained in the form of a white powder (yield=79%).
M.p.=167-170° C.
$[\alpha]_D^{31}$=−85 (c=0.22; DMSO).

EXAMPLE 48

5-Fluoro-3-Pyridinyl 2,3,4-Tri-O-Acetyl-5-Thio-β-D-Xylopyranoside

By following a procedure analogous to Example 1 and starting from 5-fluoro-3-pyridinol, the expected product is obtained in the form of a white solid (yield=20%).
M.p.=143° C.
$[\alpha]_D^{25}$=−78° (c=0.51; $CHCl_3$).

EXAMPLE 49

5-Fluoro-3-Pyridinyl 5-Thio-β-D-Xylopyranoside

By following a procedure analogous to Example 8 and starting from the compound obtained according to Example 48, the expected product is obtained in the form of a white powder (yield=85%).
M.p.=182-183° C.
$[\alpha]_D^{25}$=−95° (c=0.51; CH3OH).

EXAMPLE 50

5-Cyano-3-Pyridinyl 2,3,4-Tri-O-Acetyl-5-Thio-β-D-Xylopyranoside

By following a procedure analogous to Example 1 and starting from 5-cyano-3-pyridinol, the expected product is obtained in the form of a white solid (yield=24%).
M.p.=147° C.
$[\alpha]_D^{20}$=−3.60 (c=0.34; $CH_2Cl_2$).

EXAMPLE 51

5-Cyano-3-Pyridinyl 5-Thio-β-D-Xylopyranoside

By following a procedure analogous to Example 8 and starting from the compound obtained according to Example 50, the expected product is obtained in the form of a white solid (yield=52%).
M.p.=149° C.
$[\alpha]_D^{20}$=−30 (c=0.10; $CH_3OH$).

EXAMPLE 52

6-Chloro-3-Pyridinyl 2,3,4-Tri-O-Acetyl-5-Thio-β-D-Xylopyranoside

By following a procedure analogous to Example 1 and starting from 6-chloro-3-pyridinol, the expected product is obtained in the form of a white solid (yield=18%).
M.p.=141° C.
$[\alpha]_D^{23}$=−64° (c=0.50; $CH_2Cl_2$).

EXAMPLE 53

6-Chloro-3-Pyridinyl 5-Thio-β-D-Xylopyranoside

By following a procedure analogous to Example 8 and starting from the compound obtained according to Example 52, the expected product is obtained in the form of a white solid (yield=89%).
M.p.=218° C.
$[\alpha]_D^{23}$=−70° (c=0.50; DMSO).

EXAMPLE 54

4-Cyano-3-Pyridinyl 2,3,4-Tri-O-Acetyl-5-Thio-β-D-Xylopyranoside

By following a procedure analogous to Example 1 and starting from 4-cyano-3-pyridinol, the expected product is obtained in the form of a white solid (yield=7%).
M.p.=167° C.
$[\alpha]_D^{23}$=−148° (c=0.15; $CHCl_3$).

EXAMPLE 55

4-Cyano-3-Pyridinyl 5-Thio-β-D-Xylopyranoside

By following a procedure analogous to Example 8 and starting from the compound obtained according to Example 54, the expected product is obtained in the form of a white solid (yield=60%).
M.p.=157° C.
$[\alpha]_D^{23}$=−35° (c=0.08; DMSO).

EXAMPLE 56

5-Methyl-3-Pyridinyl 2,3,4-Tri-O-Acetyl-5-Thio-β-D-Xylopyranoside

By following a procedure analogous to Example 1 and starting from 5-methyl-3-pyridinol, the expected product is obtained in the form of cream-colored crystals (yield=11%).
M.p.=134° C.
$[\alpha]_D^{24}$=−35° (c=0.16; DMSO).

EXAMPLE 57

5-Methyl-3-Pyridinyl 5-Thio-β-D-Xylopyranoside

By following a procedure analogous to Example 8 and starting from the compound obtained according to Example 56, the expected product is obtained in the form of a white powder (yield=72%).
M.p.=213° C.
$[\alpha]_D^{25}$=−106° (c=0.20; DMSO).

EXAMPLE 58

2-Chloro-5-Fluoro-3-Pyridinyl 2,3,4-Tri-O-Acetyl-5-Thio-β-D-Xylopyranoside

By following a procedure analogous to Example 1 and starting from 2-chloro-5-fluoro-3-pyridinol, the expected product is obtained in the form of a white powder (yield=11%).
M.p.=185° C.
$[\alpha]_D^{27}$=−93° (c=0.11; DMSO).

EXAMPLE 59

2-Chloro-5-Fluoro-3-Pyridinyl 5-Thio-β-D-Xylopyranoside

By following a procedure analogous to Example 2 and starting from the compound obtained according to Example 58, the expected product is obtained in the form of a white powder (yield=65%).
M.p.=143° C.
$[\alpha]_D^{30}$=−79° (c=0.18; DMSO).

EXAMPLE 60

6-Fluoro-3-Pyridinyl 2,3,4-Tri-O-Acetyl-5-Thio-β-D-Xylopyranoside

By following a procedure analogous to Example 1 and starting from 6-fluoro-3-pyridinol, the expected product is obtained in the form of white crystals (yield=5%).
M.p.=123° C.
$[\alpha]_D^{28}$=−39° (c=0.17; DMSO).

EXAMPLE 61

6-Fluoro-3-Pyridinyl 5-Thio-β-D-Xylopyranoside

By following a procedure analogous to Example 8 and starting from the compound obtained according to Example 60, the expected product is obtained in the form of a light white solid (yield=74%).
M.p.=209-210° C.
$[\alpha]_D^{21}$=−119° (c=0.14; DMSO).

EXAMPLE 62

N-[5-[(2,3,4-Tri-O-Acetyl-5-Thio-β-D-Xylopyranosyl)Oxy]-2-Pyridinyl]Acetamide By following a procedure analogous to Example 1 and starting from N-(5-hydroxy-2-pyridinyl)acetamide, the expected product is obtained in the form of a white powder (yield=11%).
M.p.=132-133° C.
$[\alpha]^{32}{}_D$=−1.6° (c=0.20; DMSO).

EXAMPLE 63

N-[5-[(5-Thio-β-D-Xylopyranosyl)Oxy]-2-Pyridinyl]Acetamide

By following a procedure analogous to Example 2 and starting from the compound obtained according to Example 62, the expected product is obtained in the form of a white powder (yield=31%).
M.p.=209° C.
$[\alpha]_D^{25}$=−64° (c=0.40; DMSO).

EXAMPLE 64

N-[5-[(2,3,4-Tri-O-Acetyl-5-Thio-β-D-Xylopyranosyl)Oxy]-2-Pyridinyl]Methane-Sulfonamide By following a procedure analogous to Example 1 and starting from N-(5-hydroxy-2-pyridinyl)methanesulfonamide, the expected product is obtained in the form of white platelets (yield=12%).
M.p.=185-190° C.
$[\alpha]_D^{28}$=−5.5° (c=0.30; DMSO).

EXAMPLE 65

N-[5-[(5-Thio-β-D-Xylopyranosyl)Oxy]-2-Pyridinyl]Methanesulfonamide

By following a procedure analogous to Example 8 and starting from the compound obtained according to Example 64, the expected product is obtained in the form of a white powder (yield=83%).
M.p.=201-204° C.
$[\alpha]_D^{27}$=−48° (c=0.30; DMSO).

EXAMPLE 66

4-(Trifluoromethyl)-3-Pyridinyl 2,3,4-Tri-O-Acetyl-5-Thio-β-D-Xylopyranoside By following a procedure analogous to Example 1 and starting from 4-trifluoro-methyl-3-pyridinol, the expected product is obtained in the form of a white powder (yield=9%).
M.p.=198° C.
$[\alpha]_D^{32}$=−72° (c=0.27; DMSO).

EXAMPLE 67

4-(Trifluoromethyl)-3-Pyridinyl 5-Thio-β-D-Xylopyranoside

By following a procedure analogous to Example 2 and starting from the compound obtained according to Example 66, the expected product is obtained in the form of white needles (yield=60%).
M.p.=191° C.
$[\alpha]_D^{32}$=−34° (c=0.30; DMSO).

EXAMPLE 68

2-Fluoro-3-Pyridinyl 2,3,4-Tri-O-Acetyl-5-Thio-β-D-Xylopyranoside

By following a procedure analogous to Example 11 and starting from 2-fluoro-3-pyridinol, the expected product is obtained in the form of a white powder (yield=32%).

M.p.=160° C.
$[\alpha]_D^{28}$=−86° (c=0.20; CHCl$_3$).

EXAMPLE 69

2-Fluoro-3-Pyridinyl 5-Thio-β-D-Xylopyranoside

By following a procedure analogous to Example 2 and starting from the compound obtained according to Example 68, the expected product is obtained in the form of a light white solid (yield=31%).
M.p.=85-87° C.
$[\alpha]_D^{28}$=−40° (c=0.30; CH$_3$OH).

EXAMPLE 70

2,6-Dimethyl-3-Pyridinyl 2,3,4-Tri-O-Acetyl-5-Thio-β-D-Xylopyranoside
By following a procedure analogous to Example 1 and starting from 2,6-dimethyl-3-pyridinol, the expected product is obtained in the form of white powder (yield=7%).
M.p.=139-140° C.
$[\alpha]_D^{29}$=−40° (c=0.20; DMSO).

EXAMPLE 71

2,6-Dimethyl-3-Pyridinyl 5-Thio-β-D-Xylopyranoside
By following a procedure analogous to Example 8 and starting from the compound obtained according to Example 70, the expected product is obtained in the form of a white powder (yield=91%).
M.p.=186° C.
$[\alpha]_D^{26}$=−64° (c=0.20; DMSO).

EXAMPLE 72

6-Chloro-5-Fluoro-3-Pyridinyl 2,3,4-Tri-O-Acetyl-5-Thio-β-D-Xylopyranoside

By following a procedure analogous to Example 1 and starting from 6-chloro-5-fluoro-3-pyridinol, the expected product is obtained in the form of white platelets (yield=43%).
M.p.=158-162° C.
$[\alpha]_D^{27}$=−21° (c=0.30; DMSO).

EXAMPLE 73

6-Chloro-5-Fluoro-3-Pyridinyl 5-Thio-β-D-Xylopyranoside

By following a procedure analogous to Example 8 and starting from the compound obtained according to Example 72, the expected product is obtained in the form of white needles (yield=26%).
M.p.=198-200° C.
$[\alpha]_D^{31}$=−68° (c=0.10; DMSO).

EXAMPLE 74

6-Methoxy-3-Pyridinyl 5-Thio-β-D-Xylopyranoside

A mixture of 100 mg (0.8 mmol) of 6-methoxy-3-pyridinol, 568 mg (1.6 mmol) of 2,3,4-tri-O-acetyl-5-thio-β-D-xylopyranosyl bromide and 50 mg (0.16 mmol) of benzyltributylammonium chloride in 2 ml of chloroform is prepared and 552 mg (4 mmol) of potassium carbonate are added, followed by 30 μl of water. The reaction mixture is stirred for 3 hours at 50° C. and then overnight at room temperature. 8 ml of chloroform are added and the organic phase obtained is washed with water and with sodium bicarbonate solution and then dried over magnesium sulfate and concentrated under reduced pressure. The evaporation residue is taken up in 8 ml of methanol at 50° C. and filtered. The filtrate is concentrated under reduced pressure and the crude product is purified by chromatography on silica gel using a cyclohexane/ethyl acetate mixture (8/2; v/v) as the eluent to give 100 mg of a yellow oil, which is purified again by chromatography on silica gel using a dichloromethane/methanol mixture (95/5; v/v) as the eluent to give 71 mg of the expected compound in the form of a white powder (yield=22%).
M.p.=159-161° C.
$[\alpha]_D^{24}$=−98° (c=0.10; DMSO).

EXAMPLE 75

6-Cyano-5-Fluoro-3-Pyridinyl 2,3,4-Tri-O-Acetyl-5-Thio-β-D-Xylopyranoside

By following a procedure analogous to Example 5 and starting from 6-cyano-5-fluoro-3-pyridinol, the expected product is obtained in the form of a white powder (yield=38%).
M.p.=176-177° C.
$[\alpha]_D^{29}$=−37° (c=0.37; DMSO).

EXAMPLE 76

6-Cyano-5-Fluoro-3-Pyridinyl 5-Thio-β-D-Xylopyranoside

By following a procedure analogous to Example 2 and starting from the compound obtained according to Example 75, the expected product is obtained in the form of a white powder (yield=64%).
M.p.=155-156° C.
$[\alpha]_D^{29}$=−72° (c=0.44; DMSO).

EXAMPLE 77

6-Cyano-2-Methyl-3-Pyridinyl 2,3,4-Tri-O-Acetyl-5-Thio-β-D-Xylopyranoside

By following a procedure analogous to Example 1 and starting from 6-cyano-2-methyl-3-pyridinol, the expected product is obtained in the form of a white solid (yield=27%).
M.p.=128-131° C.
$[\alpha]_D^{30}$=−58° (c=0.21; DMSO).

EXAMPLE 78

6-Cyano-2-Methyl-3-Pyridinyl 5-Thio-β-D-Xylopyranoside

By following a procedure analogous to Example 2 and starting from the compound obtained according to Example 77, the expected product is obtained in the form of white needles (yield=47%).
M.p.=193-195° C.
$[\alpha]_D^{25}$=−80° (c=0.19; DMSO).

EXAMPLE 79

2-Cyano-5-Fluoro-3-Pyridinyl 2,3,4-Tri-O-Acetyl-5-Thio-β-D-Xylopyranoside

By following a procedure analogous to Example 5 and starting from 2-cyano-5-fluoro-3-pyridinol, the expected product is obtained in the form of a white solid (yield=17%).

M.p.=150° C.
$[\alpha]_D^{30}=-75°$ (c=0.30; DMSO).

EXAMPLE 80

2-Cyano-5-Fluoro-3-Pyridinyl 5-Thio-β-D-Xylopyranoside

By following a procedure analogous to Example 2 and starting from the compound obtained according to Example 79, the expected product is obtained in the form of a white solid (yield=57%).
M.p.=94° C.
$[\alpha]_D^{27}=-27°$ (c=0.30; DMSO).

EXAMPLE 81

4-Methyl-3-Pyridinyl 2,3,4-Tri-O-Acetyl-5-Thio-β-D-Xylopyranoside

By following a procedure analogous to Example 1 and starting from 4-methyl-3-pyridinol, the expected product is obtained in the form of a beige solid (yield=14%).
M.p.=150° C.
$[\alpha]_D^{30}=-65°$ (c=0.21; DMSO).

EXAMPLE 82

4-Methyl-3-Pyridinyl 5-Thio-β-D-Xylopyranoside

By following a procedure analogous to Example 2 and starting from the compound obtained according to Example 81, the expected product is obtained in the form of a white solid (yield=90%).
M.p.=236° C.
$[\alpha a]_D^{31}=-88°$ (c=0.20; DMSO).

EXAMPLE 83

6-Cyano-3-Pyridinyl 2,3,4-Tri-O-Acetyl-5-Thio-β-D-Xylopyranoside

By following a procedure analogous to Example 1 and starting from 6-cyano-3-pyridinol, the expected product is obtained in the form of a white powder (yield=24%).
M.p.=147° C.
$[\alpha]_D^{25}=-27°$ (c=0.28; DMSO).

EXAMPLE 84

6-Cyano-3-Pyridinyl 5-Thio-β-D-Xylopyranoside

By following a procedure analogous to Example 2 and starting from the compound obtained according to Example 83, the expected product is obtained in the form of a white solid (yield=77%).
M.p.=179-180° C.
$[\alpha]_D^{25}=-77°$ (c=0.25; DMSO).

EXAMPLE 85

5-(Trifluoromethyl)-3-Pyridinyl 2,3,4-Tri-O-Acetyl-5-Thio-β-D-Xylopyranoside

By following a procedure analogous to Example 1 and starting from 5-trifluoro-methyl-3-pyridinol, the expected product is obtained in the form of white crystals (yield=31%).

M.p.=111-112° C.
$[\alpha]_D^{28}=-37°$ (c=0.30; DMSO).

EXAMPLE 86

5-(Trifluoromethyl)-3-Pyridinyl 5-Thio-β-D-Xylopyranoside

By following a procedure analogous to Example 8 and starting from the compound obtained according to Example 85, the expected product is obtained in the form of a flaky white solid (yield=88%).
M.p.=160-161° C.
$[\alpha]_D^{25}=-79°$ (c=0.32; DMSO).

EXAMPLE 87

3-Pyridinyl 2,3,4-Tris-O-(Ethoxycarbonyl)-5-Thio-β-D-Xylopyranoside

A suspension of 500 mg (2.05 mmol) of the compound obtained according to Example 2 in 5 ml of tetrahydrofuran and 5 ml of acetonitrile is prepared and 25 mg (2.5 mmol) of 4-(dimethylamino)pyridine are added. 1.83 ml (12.3 mmol) of diethyl pyrocarbonate are then added gradually at room temperature, with stirring. The reaction mixture is stirred at room temperature for 7 hours and then filtered and the filtrate is concentrated under reduced pressure. The crude product is purified by chromatography on silica gel using a toluene/ethyl acetate mixture (7/3; v/v) as the eluent to give 638 mg of the expected compound in the form of a colorless oil, which crystallizes slowly (yield=67%).
M.p.=41° C.
$[\alpha]_D^{22}=-55°$ (c=0.31; $CH_2Cl_2$).

EXAMPLE 88

2-Chloro-3-Pyridinyl 2,3,4-Tris-O-(Ethoxycarbonyl)-5-Thio-β-D-Xylopyranoside

By following a procedure analogous to Example 87 and starting from the compound obtained according to Example 37, the expected product is obtained in the form of a white solid (yield=87%).
M.p.=49-52° C.
$[\alpha]_D^{25}=-78°$ (c=0.40; $CHCl_3$).

EXAMPLE 89

6-(Trifluoromethyl)-3-Pyridinyl 2,3,4-Tris-O-(Ethoxycarbonyl)-5-Thio-β-D-Xylopyranoside By following a procedure analogous to Example 87 and starting from the compound obtained according to Example 41, the expected product is obtained in the form of a white solid (yield=89%).
M.p.=55-57° C.
$[\alpha]_D^{26}=-76°$ (c=0.36; $CHCl_3$).

EXAMPLE 90

2-Cyano-3-Pyridinyl 2,3,4-Tris-O-(Ethoxycarbonyl)-5-Thio-β-D-Xylopyranoside

By following a procedure analogous to Example 87 and starting from the compound obtained according to Example 20, the expected product is obtained in the form of a colorless solid (yield=81%).

M.p.=44-48° C.
$[\alpha]_D^{25}=-76°$ (c=0.42; CHCl$_3$).

EXAMPLE 91

3-Pyridinyl 2,3,4-Tri-O-[(1-Piperidinyl)Acetyl]-5-Thio-β-D-Xylopyranoside

A mixture of 4.64 g (24.2 mmol) of EDCI [1-(3-dimethylaminopropyl)-3-ethylcarbodiimide hydrochloride] and 2.34 g (23.2 mmol) of triethylamine in 100 ml of dichloromethane is prepared and 1.22 g (5.04 mmol) of the compound obtained according to Example 2, 3.46 g (24.2 mmol) of 1-piperidineacetic acid, 3.33 g (24.7 mmol) of HOBT (1-hydroxybenzotriazole) and 0.92 g of 4-(dimethylamino)pyridine are then added, with stirring. The reaction mixture is stirred at room temperature for 20 hours and then filtered and the filtrate is washed with water (twice), dried over magnesium sulfate and concentrated under reduced pressure. The crude product is purified by chromatography on silica gel using a dichloromethane/methanol mixture (95/5; v/v) as the eluent to give an oil, which crystallizes after trituration in isopropyl ether to give 670 mg of the expected compound in the form of a white powder (yield=21%).

M.p.=116° C.
$[\alpha]_D^{28}=-21°$ (c=0.17; DMSO).

EXAMPLE 92

3-Pyridinyl 2,3,4-Tri-O-Propionyl-5-Thio-β-D-Xylopyranoside

By following a procedure analogous to Example 29 and starting from propionyl chloride, the expected product is obtained in the form of a cream-colored powder (yield=21%).

M.p.=104° C.
$[\alpha]_D^{23}=-72°$ (c=0.38; CHCl$_3$).

EXAMPLE 93

3-Pyridinyl 2,3,4-Tri-O-Butanoyl-5-Thio-β-D-Xylopyranoside

By following a procedure analogous to Example 29 and starting from butanoyl chloride, the expected product is obtained in the form of a white powder (yield=34%).

M.p.=70° C.
$[\alpha]_D^{27}=-26°$ (c=0.15; DMSO).

The structures of the compounds of formula I described above are shown in the Table below (P indicates the position of the D- or L-xylose group on the pyridine ring):

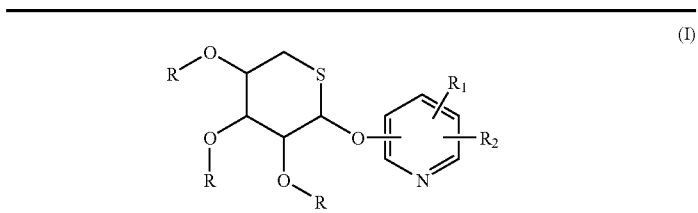

(I)

| Example | R$_1$ | R$_2$ | P | R | Salt |
|---|---|---|---|---|---|
| 1 | H | H | 3(D) | Ac | — |
| 1A | H | H | 3(D) | Ac | Ms |
| 2 | H | H | 3(D) | H | — |
| 2A | H | H | 3(D) | H | Ms |
| 2B | H | H | 3(D) | H | HSulf |
| 2C | H | H | 3(D) | H | Chlor |
| 2D | H | H | 3(D) | H | Bromh |
| 3 | H | H | 3(L) | Ac | — |
| 4 | H | H | 3(L) | H | — |
| 5 | H | H | 2(D) | Ac | — |
| 6 | H | H | 2(D) | H | — |
| 7 | H | H | 3(D) | Ac | N-Oxide |
| 8 | H | H | 3(D) | H | N-Oxide |
| 9 | H | H | 4(D) | Ac | — |
| 10 | H | H | 4(D) | H | — |
| 11 | 2-CH$_3$ | H | 3(D) | Ac | — |
| 12 | 2-CH$_3$ | H | 3(D) | H | — |
| 13 | 2-Bn | H | 3(D) | Ac | — |
| 14 | 2-Bn | H | 3(D) | H | — |
| 15 | 2-C$_2$H$_5$ | 4-CH$_3$ | 3(D) | Ac | — |
| 16 | 2-C$_2$H$_5$ | 4-CH$_3$ | 3(D) | H | — |
| 17 | 5-Cl | H | 3(D) | Ac | — |
| 18 | 5-Cl | H | 3(D) | H | — |
| 19 | 2-CN | H | 3(D) | Ac | — |
| 20 | 2-CN | H | 3(D) | H | — |
| 21 | 6-CH$_3$ | H | 3(D) | Ac | — |
| 22 | 6-CH$_3$ | H | 3(D) | H | — |
| 23 | 5-COOCH$_3$ | H | 3(D) | Ac | — |
| 24 | 5-COOCH$_3$ | H | 3(D) | H | — |
| 25 | 2-Br | H | 3(D) | Ac | — |
| 26 | 2-Br | H | 3(D) | H | — |
| 27 | 2-NO$_2$ | H | 3(D) | Ac | — |
| 28 | 2-NO$_2$ | 6-CH$_3$ | 3(D) | Ac | — |
| 29 | H | H | 3(D) | (CH$_3$)$_2$CHCO | — |

-continued

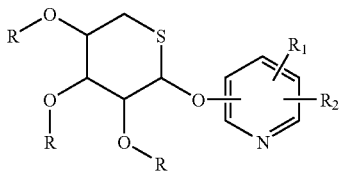

(I)

| Example | R₁ | R₂ | P | R | Salt |
|---|---|---|---|---|---|
| 29A | H | H | 3(D) | (CH₃)₂CHCO | Ms |
| 30 | H | H | 3(D) | (CH₃)₂CH—CH₂—CO | |
| 30A | H | H | 3(D) | (CH₃)₂CH—CH₂—CO | Ms |
| 31 | H | H | 3(D) | COOCH₃ | |
| 31A | H | H | 3(D) | COOCH₃ | Chlor |
| 31B | H | H | 3(D) | COOCH₃ | Ms |
| 32 | H | H | 3(D) | H | Cl⁻ Quatern |
| 33 | H | H | 3(D) | CO—C(CH₃)₃ | Piv |
| 34 | 6-CH₃ | H | 2(D) | Ac | — |
| 35 | 6-CH₃ | H | 2(D) | H | — |
| 36 | 2-Cl | H | 3(D) | Ac | — |
| 37 | 2-Cl | H | 3(D) | H | — |
| 38 | 2-CH₂—N(CH₃)₂ | H | 3(D) | Ac | — |
| 39 | 2-CH₂—N(CH₃)₂ | H | 3(D) | H | — |
| 40 | 6-CF₃ | H | 3(D) | Ac | — |
| 41 | 6-CF₃ | H | 3(D) | H | — |
| 42 | 5-Cl | 2-CN | 3(D) | Ac | — |
| 43 | 5-Cl | 2-CN | 3(D) | H | — |
| 44 | 4-CN | 2-CH₃ | 3(D) | Ac | — |
| 45 | 4-CN | 2-CH₃ | 3(D) | H | — |
| 46 | 2-F | 6-CH₃ | 3(D) | Ac | |
| 47 | 2-F | 6-CH₃ | 3(D) | H | |
| 48 | 5-F | H | 3(D) | Ac | — |
| 49 | 5-F | H | 3(D) | H | — |
| 50 | 5-CN | H | 3(D) | Ac | — |
| 51 | 5-CN | H | 3(D) | H | — |
| 52 | 6-Cl | H | 3(D) | Ac | — |
| 53 | 6-Cl | H | 3(D) | H | — |
| 54 | 4-CN | H | 3(D) | Ac | — |
| 55 | 4-CN | H | 3(D) | H | — |
| 56 | 5-CH₃ | H | 3(D) | Ac | — |
| 57 | 5-CH₃ | H | 3(D) | H | — |
| 58 | 2-Cl | 5-F | 3(D) | Ac | — |
| 59 | 2-Cl | 5-F | 3(D) | H | — |
| 60 | 6-F | H | 3(D) | Ac | — |
| 61 | 6-F | H | 3(D) | H | — |
| 62 | 6-NH—CO—CH₃ | H | 3(D) | Ac | — |
| 63 | 6-NH—CO—CH₃ | H | 3(D) | H | — |
| 64 | 6-NH—SO₂—CH₃ | H | 3(D) | Ac | — |
| 65 | 6-NH—SO₂—CH₃ | H | 3(D) | H | — |
| 66 | 4-CF₃ | H | 3(D) | Ac | — |
| 67 | 4-CF₃ | H | 3(D) | H | — |
| 68 | 2-F | H | 3(D) | Ac | — |
| 69 | 2-F | H | 3(D) | H | — |
| 70 | 2-CH₃ | 6-CH₃ | 3(D) | Ac | — |
| 71 | 2-CH₃ | 6-CH₃ | 3(D) | H | — |
| 72 | 5-F | 6-Cl | 3(D) | Ac | — |
| 73 | 5-F | 6-Cl | 3(D) | H | — |
| 74 | 6-OCH₃ | H | 3(D) | H | |
| 75 | 5-F | 6-CN | 3(D) | Ac | |
| 76 | 5-F | 6-CN | 3(D) | H | |
| 77 | 2-CH₃ | 6-CN | 3(D) | Ac | |
| 78 | 2-CH₃ | 6-CN | 3(D) | H | |
| 79 | 2-CN | 5-F | 3(D) | Ac | |
| 80 | 2-CN | 5-F | 3(D) | H | |
| 81 | 4-CH₃ | H | 3(D) | Ac | |
| 82 | 4-CH₃ | H | 3(D) | H | |
| 83 | 6-CN | H | 3(D) | Ac | |
| 84 | 6-CN | H | 3(D) | H | |
| 85 | 5-CF₃ | H | 3(D) | Ac | |
| 86 | 5-CF₃ | H | 3(D) | H | |
| 87 | H | H | 3(D) | —COOC₂H₅ | |
| 88 | 2-Cl | H | 3(D) | —COOC₂H₅ | |
| 89 | 6-CF₃ | H | 3(D) | —COOC₂H₅ | |
| 90 | 2-CN | H | 3(D) | —COOC₂H₅ | |

-continued (I)

| Example | R₁ | R₂ | P | R | Salt |
|---|---|---|---|---|---|
| 91 | H | H | 3(D) | —COCH₂-Pip | |
| 92 | H | H | 3(D) | —COC₂H₅ | |
| 93 | H | H | 3(D) | —COC₃H₇ | |

Ac = acetyl
Bn = benzyl (phenylmethyl)
Pip = 1-piperazinyl
Ms = methanesulfonate
Chlor = hydrochloride
Bromh = hydrobromide
Quatern = quaternary pyridinium salt
HSulf = hemisulfate
Piv = pivalate The antithrombotic activity of the compounds according to the invention was studied in vivo in the rat by means of a test that reproduces a venous thrombosis.

The venous thrombosis was induced according to the protocol described in *Thromb. Haemost.*, 1992, 67(1), 176-179. The intravenous or oral activity was studied according to the following operating protocol:

The experiments are performed on non-fasted Wistar male rats weighing 250 to 280 g, divided into groups of 10 animals each. The test products are administered either orally (tubage) dissolved or suspended in isotonic solution, or by intravenous injection dissolved in isotonic solution or in a PEG 400/water mixture. The concentration of the compounds is calculated so that the amount of solution absorbed is 2 ml/kg by oral administration and 1 ml/kg by intravenous injection. A thrombosis is induced at a time T (0.5, 2, 4 or 8 hours) after administration of the product, and the thrombus formed is removed and weighed. To induce this thrombosis, a venous stasis is created under hypercoagulation according to the technique described by WESSLER (*J Applied Physiol.*, 1959, 943-946), the hypercoagulating agent used being a solution of activated factor X (Xa) having a concentration of 7.5 nKat/kg, supplied by Biogenic (Montpellier). The venous stasis is effected exactly 15 seconds after injection of the hypercoagulating agent. The activity of the test compounds was checked at different doses after they had been administered either orally (p.o.) or intravenously (i.v.). The thrombosis was induced 2 hours or 4 hours after oral administration of the compound and 2 hours after intravenous administration of the compound. By way of example, the results of the above tests are shown in the Tables below for a few compounds according to the invention (the activity is expressed as the percentage inhibition of thrombus formation observed in the presence of the compound according to the invention, relative to the weight of the thrombus formed in the absence of the compound).

TABLE I

Oral activity

| Example | Dose (mg/kg) | Time (h) | Activity % |
|---|---|---|---|
| 1A | 6 | 4 | 51 |
| 2 | 3 | 4 | 91 |
| 2 | 1.5 | 4 | 67 |
| 2C | 6 | 4 | 55 |
| 2A | 4.2 | 2 | 96 |
| 12 | 3 | 4 | 52 |
| 18 | 3 | 4 | 46 |
| 20 | 3 | 4 | 50 |
| 31A | 5.6 | 4 | 63 |
| 31B | 8 | 4 | 94 |
| 36 | 6 | 2 | 91 |
| 37 | 6 | 2 | 96 |
| 41 | 6 | 2 | 97 |
| 49 | 6 | 2 | 90 |
| 93 | 6 | 2 | 81 |

TABLE II

Intravenous activity

| Example | Dose (mg/kg) | Time (h) | Activity % |
|---|---|---|---|
| 1A | 4 | 2 | 83 |
| 2 | 2.5 | 2 | 72 |
| 2A | 2.5 | 2 | 68 |
| 2A | 5 | 2 | 94 |
| 2C | 2.5 | 2 | 72 |
| 2C | 4 | 2 | 95 |
| 31B | 5 | 2 | 88 |

The results show that the compounds according to the invention exhibit a venous antithrombotic activity by both oral and intravenous administration.

The present invention therefore relates to a compound of formula (I) according to the invention, and its pharmaceutically acceptable salts with an acid, solvates and hydrates, for use as drugs. The compound of formula (I), or one of its pharmaceutically acceptable salts, solvates or hydrates, may be used for the preparation of an antithrombotic drug intended in particular for the treatment or prevention of disorders of the venous circulation and especially for correcting certain hematological parameters perceptible in the venous system.

The present invention therefore further relates to pharmaceutical compositions containing a compound of formula (I) or one of its pharmaceutically acceptable salts, solvates or hydrates. These pharmaceutical compositions generally contain suitable excipients. Said excipients are chosen according to the desired pharmaceutical form and the desired mode of administration, particularly oral administration or administration by injection.

These pharmaceutical compositions are prepared by the conventional methods well known to those skilled in the art. For example, the compounds according to the invention can be formulated with physiologically acceptable excipients to give an injectable form for direct use, an injectable form to be prepared immediately before use, or a solid form for oral administration, for example a gelatin capsule or a tablet.

By way of example, an injectable form can preferably be prepared by the lyophilization of a sterilized filtered solution containing the compound according to the invention and a soluble excipient in a necessary and sufficient amount to give an isotonic solution after the addition of injectable water immediately before use. An oral form will preferably be presented in the form of a gelatin capsule containing the finely ground or, preferably, micronized compound of the invention mixed with excipients known to those skilled in the art, for example lactose, pregelatinized starch and magnesium stearate.

To obtain the desired therapeutic or prophylactic effect, each unit dose can contain 10 to 500 mg of at least one compound according to the invention.

The invention claimed is:

1. Thioxylose compounds, wherein the compounds are selected from:
   a) the compounds of the formula

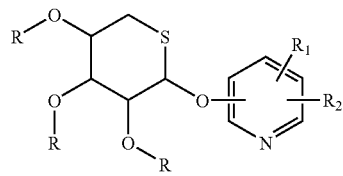

I in which:
   the pentapyranosyl group is a 5-thio-β-D-xylopyranosyl group or a 5-thio-β-L-xylopyranosyl group,
   R is a hydrogen atom, a $C_2$-$C_6$ acyl group, an acetyl group substituted by a nitrogen heterocycle, or a group —COOR',
   $R_1$ and $R_2$ independently of one another are each a hydrogen atom, a halogen atom, a cyano, nitro or trifluoromethyl group, a $C_1$-$C_4$ alkyl group optionally substituted by an aromatic ring, a group —COOR', a group —CH$_2$—NR'R", a $C_1$-$C_4$ alkoxy group, a group —NH—CO—R' or a group —NH—SO$_2$—R', and
   R' and R" independently are each a $C_1$-$C_4$ alkyl group; and
   b) their addition salts, oxides or quaternary ammonium salts.

2. Compound according to claim 1, wherein the pentapyranosyl group is a 5-thio-β-D-xylopyranosyl group or a 5-thio-β-L-xylopyranosyl group,
   R is a hydrogen atom, a $C_2$-$C_6$ acyl group or a group —COOR', R' is a $C_1$-$C_3$ alkyl group, and
   $R_1$ and $R_2$ independently of one another are each a hydrogen atom, a halogen atom, a cyano, nitro or trifluoromethyl group or a $C_1$-$C_4$ alkyl group optionally substituted by an aromatic ring.

3. Compound according to claim 1, wherein the pentapyranosyl group is the 5-thio-β-D-xylopyranosyl group.

4. Compound according to claim 1, wherein the pentapyranosyl group is in the 3-position of the pyridine heterocycle.

5. Compound according to claim 1, wherein $R_1$ and $R_2$ are a hydrogen atom.

6. Compound according to claim 1, wherein R is a hydrogen atom.

7. Compound according to claim 1, wherein R is a group —COCH$_3$, a group —COOCH$_3$ or a group —COOC$_2$H$_5$.

8. Process for the manufacture of a compound according to claim 1, wherein the process comprises:
   a) reacting a pyridinol of the formula

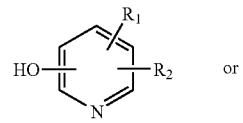

II or

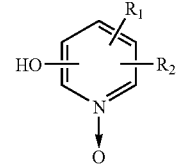

IIa in which:
   $R_1$ and $R_2$ independently of one another are each a hydrogen atom, a halogen atom, a cyano, nitro or trifluoromethyl group, a $C_1$-$C_4$ alkyl group optionally substituted by an aromatic ring, a group —COOR', a group —CH$_2$—NR'R", a $C_1$-$C_4$ alkoxy group, a group —NH—CO—R' or a group —NH—SO$_2$—R', and
   R' and R" independently are each a $C_1$-$C_4$ alkyl group, with a 5-thioxylopyranose derivative of the formula

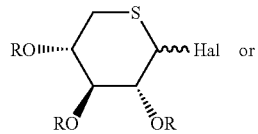

(III-D)

or

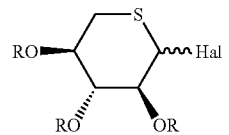

(III-L)

in which Hal is a halogen, preferably bromine, and R is a $C_2$-$C_6$ acyl group, in an aprotic solvent, in the presence of a silver salt or a zinc salt, in an anhydrous medium, at a tem perature of between 25 and 80° C., for 1 to 10 hours, to give the compound of formula I or the corresponding N-oxide:

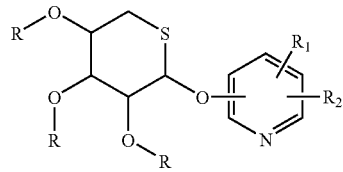

I in which the pentapyranose group is D- or L-5-thioxylopyranose and R, $R_1$ and $R_2$ are as defined in the starting compounds;

b) if necessary, reacting the compound of formula I obtained above with a solution of ammonia in methanol to give the compound of the formula

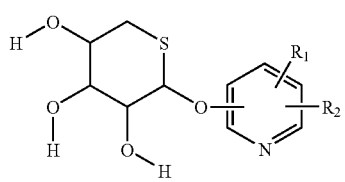

Ia in which $R_1$ and $R_2$ are as defined above; and c) if necessary, reacting one of the compounds obtained above, I or Ia, with an acid to give the corresponding addition salt; or d) if necessary, reacting one of the compounds obtained above, of formula I or Ia, with an organic halide to give the corresponding ammonium salt.

9. Process for the manufacture of a compound according to claim 1, wherein the process comprises:

a) reacting the tetra-O-acetyl-5-thioxylopyranose of the formula:

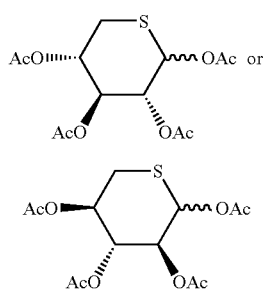

(IV-D)

(IV-L)

in which Ac is the acetyl group, with a compound of the formula

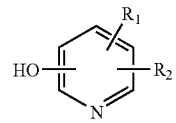

II in which:

$R_1$ and $R_2$ independently of one another are each a hydrogen atom, a halogen atom, a cyano, nitro or trifluoromethyl group, a $C_1$-$C_4$ alkyl group optionally substituted by an aromatic ring, a group —COOR', a group —$CH_2$—NR'R'', a $C_1$-$C_4$ alkoxy group, a group —NH—CO—R' or a group —NH—SO$_2$—R', and R' and R'' independently are each a $C_1$-$C_4$ alkyl group, in an aprotic solvent, in the presence of a catalyst of the Lewis acid type, at a temperature of between 20 and 60° C., for 1 to 2 hours, to give the compound of the formula

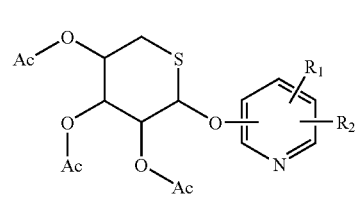

Ib in which $R_1$ and $R_2$ are as defined in the starting compounds;

b) if necessary, reacting the compound of formula I obtained above with sodium methylate in methanol to give the compound of the formula

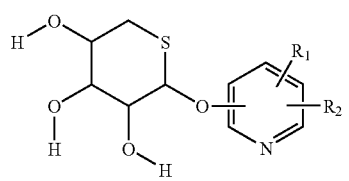

Ia in which $R_1$ and $R_2$ are as defined above; and c) if necessary, reacting one of the compounds obtained above, I or Ia, with an acid to give the corresponding addition salt.

10. Compound according to claim 1, wherein the compound is a drug.

11. Method for treating thromboses in a patient in need thereof, said method comprising administering to said patient a therapeutically effective amount of a compound according to claim 1.

12. The method according to claim 11, wherein the thromboses comprises venous thromboses.

* * * * *

UNITED STATES PATENT AND TRADEMARK OFFICE
CERTIFICATE OF CORRECTION

PATENT NO. : 7,470,671 B2  
APPLICATION NO. : 10/572999  
DATED : December 30, 2008  
INVENTOR(S) : Barberousse et al.

It is certified that error appears in the above-identified patent and that said Letters Patent is hereby corrected as shown below:

Title Page, (73) Assignee: Laboratoire Fournier should read Laboratoires Fournier S.A.

Signed and Sealed this

Twenty-fifth Day of August, 2009

David J. Kappos  
*Director of the United States Patent and Trademark Office*

UNITED STATES PATENT AND TRADEMARK OFFICE
CERTIFICATE OF CORRECTION

PATENT NO. : 7,470,671 B2
APPLICATION NO. : 10/572999
DATED : December 30, 2008
INVENTOR(S) : Barberousse et al.

It is certified that error appears in the above-identified patent and that said Letters Patent is hereby corrected as shown below:

Column 1, line 20:
"glycosarinoglycans" should read "glycosaminoglycans"

Column 5, line 30:
The end of the sentence is missing and should read as follows: "... for 1 to 2 hours to give the compound of the formula"

Column 7, line 46:
"dichioromethane" should read "dichloromethane"

Column 12, line 14:
"$[\alpha]_D^{32} = +950$" should read "$[\alpha]_D^{32} = +95°$"

Column 15, line 33:
"$[\alpha]_D^{23} = -43$" should read "$[\alpha]_D^{23} = -43°$"

Column 17, line 64 and column 18, line 66:
"A" should be "Å" or "Angstroms"

Column 21, line 34:
"$[\alpha]_D^{31} = -85$" should read "$[\alpha]_D^{31} = -85°$"

Column 21, last line:
"$[\alpha]_D^{20} = +3.60$" should read "$[\alpha]_D^{20} = +3.6°$"

Column 22, line 10:
"$[\alpha]_D^{20} = -30$" should read "$[\alpha]_D^{20} = +3°$"

Column 23, last line:
"$[\alpha]^{32}D$" should read "$[\alpha]^{32}_D$"

Column 24, line 16:
"Methane-Sulfonamide" should read "Methanesulfonamide"

Signed and Sealed this
Thirtieth Day of August, 2011

David J. Kappos
*Director of the United States Patent and Trademark Office*

Column 24, line 43:

"4-trifluoro-methyl" should read "4-trifluoromethyl"

Column 25, line 15-21:

The title should be centered and a line should be inserted between the title and the following paragraph.

Column 25, lines 25-26:

A line should be inserted between the title and the following paragraph.

Column 25, line 61:

"...-5-thio-60-D..." should read "...-5-thio-α-D-...".

Column 25, line 65:

The "," after the figure 30 should be deleted

Column 27, line 36:

"$[\alpha a]_D^{31}$" should read "$[\alpha]_D^{31}$"